United States Patent
Su et al.

(10) Patent No.: US 7,232,922 B2
(45) Date of Patent: Jun. 19, 2007

(54) METHOD FOR PREPARING ARYLPHOSPHONITE ANTIOXIDANT

(75) Inventors: Wen-Chiung Su, Taipei (TW); Tseng-Rong Wu, Yonghe (TW); Chin-Shang Sheng, Longtan Township, Taoyuan County (TW)

(73) Assignee: Chung Shan Institute of Science & Technology, Taoyuan (TW)

( * ) Notice: Subject to any disclaimer, the term of this patent is extended or adjusted under 35 U.S.C. 154(b) by 441 days.

(21) Appl. No.: 10/983,620

(22) Filed: Nov. 9, 2004

(65) Prior Publication Data

US 2005/0184277 A1    Aug. 25, 2005

(30) Foreign Application Priority Data

Feb. 19, 2004    (TW) ............... 93104131 A

(51) Int. Cl.
*C07F 9/02*    (2006.01)
(52) U.S. Cl. ....................................... 558/82
(58) Field of Classification Search ............ 558/82
See application file for complete search history.

(56) References Cited

U.S. PATENT DOCUMENTS

2004/0204602 A1* 10/2004 Lin et al. .............. 558/82

\* cited by examiner

*Primary Examiner*—Joseph K. McKane
*Assistant Examiner*—Rei-tsang Shiao
(74) *Attorney, Agent, or Firm*—Bacon & Thomas, PLLC

(57) ABSTRACT

A method for preparing an arylphosphonite antioxidant of the formula (I) below is disclosed,

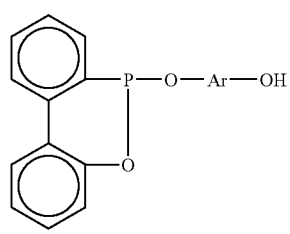
(I)

wherein Ar is

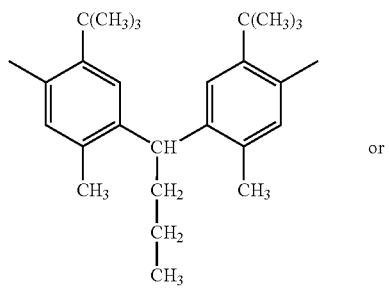

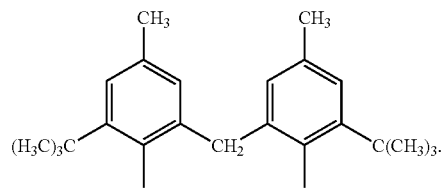

First, the reactants 2-phenylphenol and phosphorus trichloride are heated under the existence of a zinc chloride catalyst for producing 6-chloro-6H-dibenz[c,e][1,2]oxaphosphorin (CDOP) of the formula (II) below:

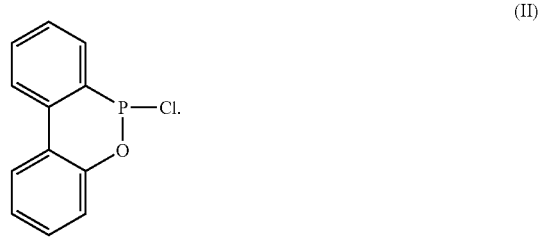

(II)

Next, the excess phosphorus trichloride is removed. Finally, an organic solution of a di-hydroxylphenol compound of the formula (III), Ar—(OH)$_2$    (III)

wherein Ar is defined as the above, is heated with the CDOP of formula (II) to form the product of the formula (I).

5 Claims, No Drawings

METHOD FOR PREPARING ARYLPHOSPHONITE ANTIOXIDANT

BACKGROUND OF THE INVENTION

1. Field of the Invention

The present invention relates to a method for preparing the arylphosphonite antioxidant and, more particularly, to a method for preparing the bifunctional arylphosphonite antioxidant that has both the first grade and second grade anti-oxidation functions.

2. Description of the Related Prior Art

The uses of antioxidants are to retard or forbid oxidation of plastic materials, thereby extends the usage time of the materials. At present, the main classification of antioxidants is hindered phenols, phosphites, thioethers. Hindered phenol is the most popular first grade antioxidant. Taking 1010 and 1076 as stand for the macromolecular hindered phenols, where the market consumption of them unceasingly increases, and in recent years the trend of domestic production rate of 1010 and 1076 are doubling. Aside from the first grade antioxidants, the second grade antioxidants TNPP and 168 are the chief products of phosphites, the manufacturing techniques of TNPP and 168 are fully developed at the same time and market is stable. There are dialkylthiodipropionate of thioethers auxiliary antioxidants that are still in production in industry, therefore the variety of thioethers auxiliary antioxidant are much simpler with respect to other groups.

However, the aforementioned antioxidants consist only of single anti-oxidation function, they can only either be first grade or second grade antioxidant but not both.

SUMMARY OF THE INVENTION

The present invention is to provide a method for preparing an arylphosphonite antioxidant with high selectivity and high conversion. The product of the present invention is a useful antioxidant in a high temperature plastic fabrication process. The arylphosphonite antioxidant of the present invention is a bifunctional arylphosphonite antioxidant that has both the first grade and second grade anti-oxidation functions.

The present invention provides a method for preparing an arylphosphonite antioxidant of the formula (I)

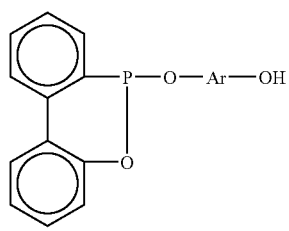
(I)

wherein Ar is

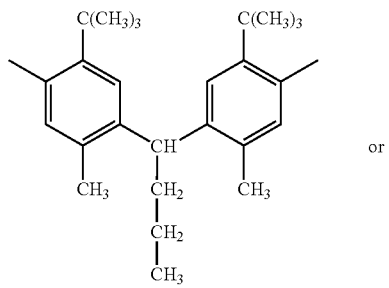
or
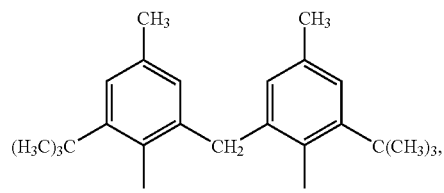

which comprising:

(a) heating a 2-phenylphenol compound with a phosphorus trichloride compound in the present of a zinc chloride catalyst to obtain a 6-chloro-6H-dibenz[c,e][1,2]oxaphosphorin of the following formula (II):

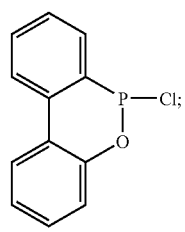
(II)

(b) removing the excess phosphorus trichloride; and (c) heating an organic solution of a di-hydroxylphenol of the following formula (III),

Ar—(OH)$_2$ (III)

wherein Ar is defined the same as the above formula (I), with the 6-chloro-6H-dibenz[c,e][1,2]oxaphosphorin (CDOP) of formula (II) to form the bifunctional arylphosphonite antioxidant of formula (I).

In the above method, the molar ratio of the 2-phenylphenol compound to the phosphorus trichloride compound in step (a) is preferably between 1:1.1 to 1:1.2. The heating temperature in step (a) is preferably between 30 to 200° C. The heating temperature in step (c) is preferably between 80 to 150° C. The organic solution in step (c) is preferably toluene or chlorobenzene.

DETAILED DESCRIPTION OF THE PREFERRED EMBODIMENTS

The structure of the arylphosphonite antioxidant of the present invention is illustrated as the formula (I) below:

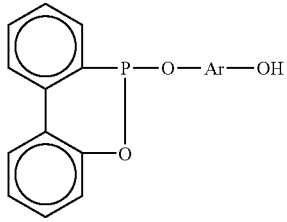
(I)

wherein, Ar is

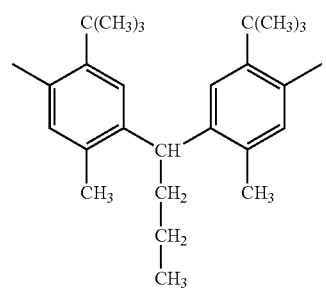

or

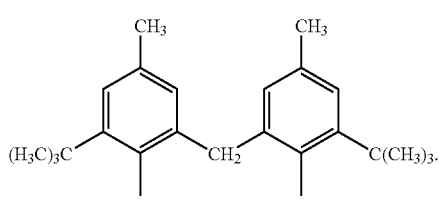

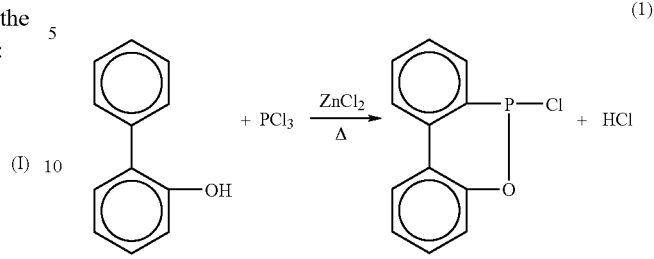
(1)

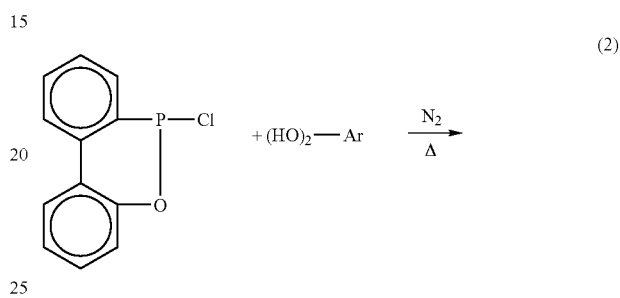
(2)

$(HO)_2$—Ar:

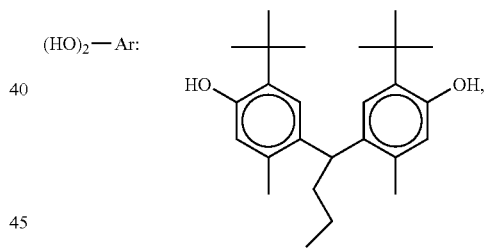

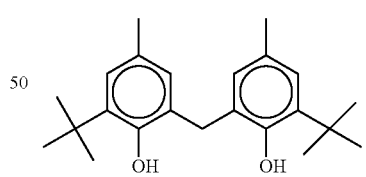

According to the present invention, the preparation of the arylphosphonite antioxidant is performed in an one-pot reactor. First of all, excessive phosphorous trichloride, 2-phenylphenol, and a trace amount of zinc chloride catalyst are put into the reactor and heated to proceed the first stage esterification and intramolecular cyclization reaction. The reaction temperature preferably between 30° C. and 200° C. The reaction equation of the esterification and cyclization are shown as the reaction equation (1). Whether the reaction is completed or not, it is determined by a $^{31}P$ nuclear resonance spectroscopy. After the excessive phosphorous trichloride is recovered by vacuum distillation, the 6-chloro-6H-dibenz[c,e][1,2]oxaphosphorin (CDOP) is obtained.

As soon as the temperature is cooled to room temperature, CDOP can further proceed with the second stage esterification by reacting with an organic solution of a diphenol compound in the presence of heat. The second stage esterification can be shown as the above reaction equation (2). The reaction temperature of the second stage esterification is preferably between 80~150° C. The arylphosphonite antioxidant of the present invention is suitable for applying on polyolefin.

Examples of the arylphosphonite antioxidant of the present invention are listed below:

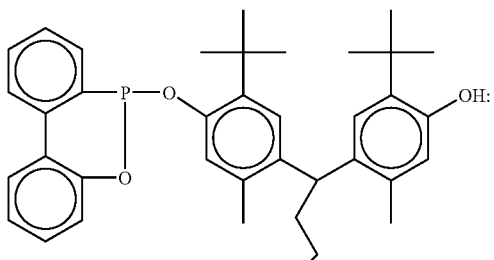

TBBP 6-(4,4'-butylidene-2-t-butyl-5-methylphenol-2'-t-butyl-5'-methylphenoxy)dibenz[c,e][1,2]oxaphosphorine

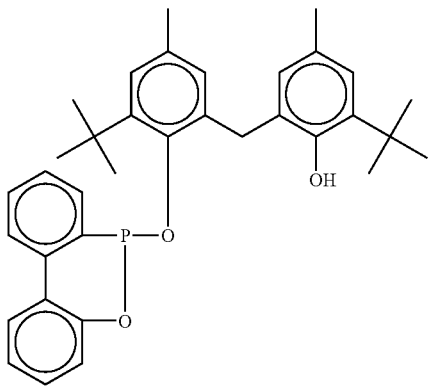

TMBP 6-(2,2'-methylene-6-t-butyl-4-methylphenol-6'-t-butyl-4'-methylphenoxy)dibenz[c,e][1,2]oxaphosphorine More detailed examples are used to illustrate the present invention, and these examples are used to explain the present invention. The examples below, which are given simply by way of illustration, must not be taken to limit the scope of the invention.

EXAMPLE 1

170 g (1 mole) of 2-phenylphenol, 151 g (1.1 mole) of phosphorous trichloride and 1.36 g (0.0.1 mole) of zinc chloride as a catalyst are weighted out and mixed together at the same instance inside a 2 liter reactor. A distillate storage tank equipped with a pressure equilibrium tube and a control valve is installed between the reactor and the condenser, the condenser is controlled at 0° C. while a gas inlet is attached above the condenser. On the other end of the gas inlet is a drying tube and the gas inlet is further connected to a neutralization tank. The reaction starts when the temperature of the reacting fluid is approximately at 30° C., with the temperature being maintained at 60~80° C. throughout, about an hour later hydrochloric acid gas produced due to the reaction will starts to retard. Follow by the aforesaid reaction the temperature of esterification is further elevated, where phosphorous trichloride is distilled continuously and its distillates are stored in a storage reservoir. At the instance the reacting fluid reached 110° C., one can starts to retrieve phosphorous trichloride from the distillate storage tank, while the temperature is free to elevate until it reaches 180° C. Four hours later, hydrochloric acid gas will tend to an end, and it can be concluded that the intramolecular cyclization is completed. Whether the reaction is completed or not, it is determined by a $^{31}$P nuclear resonance spectroscopy. The excessive phosphorous trichloride can be recovered by vacuum distillation. The 6-chloro-6H-dibenz[c,e][1,2]oxaphosphorin (CDOP) is obtained.

Next, the temperature is set back to room temperature and a diphenol solution is obtained by dissolving 382 g (1 mole) of 4,4'-butylidenebis(2-t-butyl-5-methylphenol) in 1000 ml of toluene solution. The diphenol solution is used to conduct into the 6-chloro-6H-dibenz[c,e][1,2]oxaphosphorin (CDOP) for proceeding with the second stage esterification. The resultant solution is reflux for 12 hours with nitrogen gas conducting into the solution for an hour, and upon reaction completion the room temperature is set back again. Subsequently, a stream of ammonia gas is first conducted into the solution for 5 minutes then filtered, and toluene is recovered which left TBBP as the only initial product. The product is determined by $^{31}$P nuclear resonance spectroscopy whether CDOP is complete esterification, also through the gel permeation chromatographic analysis it is analyzed that the selectivity of TBBP is around 90%. Moreover the initial product is separated into pure product TBBP by liquid chromatography where toluene is used as an eluent.

TBBP spectrum: $^{31}$P NMR Spectrometer δ 124.1 (d, J=12 Hz), $^{1}$H NMR Spectrometer δ 7.1~8.1(11H, m), δ 6.5(1H, s), δ 4.2(1H, t, J=9 Hz), δ 2.4(3H, s), δ 2.2(3H, s), δ 1.9(2H, m), δ 1.4(9H, s), δ 1.3(2H, m), δ 1.1(9H, s), δ 1.0(3H, t, J=7.5 Hz). IR spectrum: 3510 cm$^{-1}$ (—OH), mass spectrum: 580[M] 537[M-C$_3$H$_7$] 199 [basepeak, biphenylphosphorin], TGA: 300° C. (85%) 400° C. (40%).

EXAMPLE 2

The first stage esterification of the present example is the same as example 1. The second stage diphenol solution is prepared by dissolving 1 mole (340 g) of 2,2'-methylenebis (6-t-butyl-4-methylphenol) in 1000 ml of chlorobenzene solution. The diphenol solution is then conducted into TBBP under thermal reaction and it is reflux for 20 hours. Next, a stream of nitrogen gas is conducted into the solution for an hour, and upon reaction completion the temperature is raised back to room temperature. Subsequently, a stream of ammonia gas is conducted into the solution interface for 5 minutes, then it is filtered and chlorobenzene is recovered leaving TMBP as the sole initial product. The product is determined by $^{31}$P nuclear resonance spectroscopy whether CDOP is complete esterification, also through gel permeation chromatographic analysis, it is analyzed that the selectivity of TMBP is roughly 80%. By liquid chromatographic separated with ethyl acetate being its eluent, pure TMBP is obtained.

TMBP spectrum: $^{31}$P NMR Spectrometer: δ 134.2 (d, J=12 Hz), $^{1}$H NMR Spectrometer: δ 7.1~8.1(12H, m), δ 4.1(2H, s), δ 2.3(6H, s), δ 1.5(9H, s), δ 1.4(9H, s). IR spectrum: 3490 cm$^{-1}$ (—OH), mass spectrum: 538[M] 199 [basepeak, biphenylphosphorin], TGA: 300° C. (75%) 400° C. (15%).

EXAMPLE 3

Obtain and mix PP powder (Yung Chia Chem. Ind. Co. NO. 2020) with 1200 ppm of calcium stearic acid (relative weight), then the mixed powder is added separately into 1000 ppm of TBBP initial product, TBBP pure product, TMBP initial product, TMBP pure product, as well as comparative example [1000 ppm of first grade antioxidant 1010 (tetrakis(3-(3,5-di-t-butyl-4-hydroxyphenyl)propionyloxymethyl)methane) and 1000 ppm of second grade antioxidant 168 (tris(2,4-di-t-butylphenyl)phosphite)]. After the powder is blended in a mixer at 200° C., melt index (MI) is extruded 5 times at 230° C. and yellowness index (YI) test pieces were then molded by injection molding at 250° C., where the data is shown in table 1.

As demonstrated in table 1 below, when the bifunctional arylphosphonite antioxidant of the present invention comes across high temperature processing, the potency is more apparent with respect to common antioxidants.

TABLE 1

| PP | | 1st trial | 2nd trial | 3rd trial | 4th trial | 5th trial |
|---|---|---|---|---|---|---|
| Melt index (MI) g/10 min | TBBP initial product | 3.1 | 3.2 | 3.1 | 3.2 | 3.4 |
| | TBBP pure product | 3.0 | 3.1 | 3.1 | 3.2 | 3.3 |
| | TMBP initial product | 3.4 | 3.5 | 3.5 | 3.7 | 3.9 |
| | TMBP pure product | 3.1 | 3.1 | 3.2 | 3.3 | 3.3 |
| | Comparative example | 4.6 | 4.6 | 5.3 | 5.4 | 5.6 |
| Yellowness index (YI) | TBBP initial product | −4.14 | −3.74 | −3.22 | −2.85 | −2.45 |
| | TBBP pure product | −4.52 | −4.21 | −4.02 | −3.81 | −3.54 |
| | TMBP initial product | −4.04 | −3.62 | −3.11 | −2.75 | −2.32 |
| | TMBP pure product | −4.41 | −4.10 | −3.80 | −3.62 | −3.31 |
| | Comparative example | −3.60 | −3.40 | −2.30 | −0.85 | 0.20 |

PREPARATION EXAMPLE 4

Obtain and mix PE powder (Formosa Plastics Co. Formosa 9003) with 1,200 ppm of calcium stearic acid (relative weight), then the mixed powder is added separately into 1000 ppm of TBBP initial product, TBBP pure product, TMBP initial product, TMBP pure product, as well as comparative example (1000 ppm of first grade antioxidant 1010 and 1000 ppm of second grade antioxidant 168). At approximately 180° C. the powder is blended in a mixer, where melt index (MI) and yellowness index (YI) are extruded 5 times at 200° C., where the data are shown in table 2.

As demonstrated from table 2, the bifunctional arylphosphonite antioxidant of the present invention when encountered low temperature processes the melt index changes slightly, but yellowness index still indicate that the bifunctional arylphosphonite antioxidant is more preferable.

TABLE 2

| PE | | 1st trial | 2nd trial | 3rd trial | 4th trial | 5th trial |
|---|---|---|---|---|---|---|
| Melt index (MI) g/10 min | TBBP initial product | 0.26 | 0.26 | 0.27 | 0.27 | 0.28 |
| | TBBP pure product | 0.25 | 0.25 | 0.24 | 0.24 | 0.23 |
| | TMBP initial product | 0.26 | 0.26 | 0.25 | 0.25 | 0.24 |
| | TMBP pure product | 0.25 | 0.25 | 0.24 | 0.23 | 0.23 |
| | Comparative example | 0.25 | 0.24 | 0.23 | 0.21 | 0.20 |
| Yellowness index (YI) | TBBP initial product | −2.21 | −2.01 | −1.86 | −1.43 | −1.07 |
| | TBBP pure product | −2.30 | −2.21 | −2.10 | −1.75 | −1.43 |

TABLE 2-continued

| PE | | 1st trial | 2nd trial | 3rd trial | 4th trial | 5th trial |
|---|---|---|---|---|---|---|
| | TMBP initial product | −1.98 | −1.84 | −1.62 | −1.38 | −1.02 |
| | TMBP pure product | −2.10 | −2.01 | −1.84 | −1.52 | −1.14 |
| | Comparative example | −2.12 | −1.54 | −1.02 | −0.46 | −0.02 |

The arylphosphonite antioxidant of the present invention is a bifunctional arylphosphonite antioxidant that has both the first grade and second grade anti-oxidation functions. From the above experiments, the arylphosphonite antioxidant of the present invention is proven that this new compound has both the first grade and second grade traditional antioxidant's superior performance.

Although the present invention has been explained in relation to its preferred embodiment, it is to be understood that many other possible modifications and variations can be made without departing from the scope of the invention as hereinafter claimed.

What is claimed is:

1. A method for preparing an arylphosphonite antioxidant of the following formula (I):

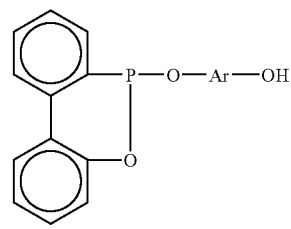

wherein Ar is

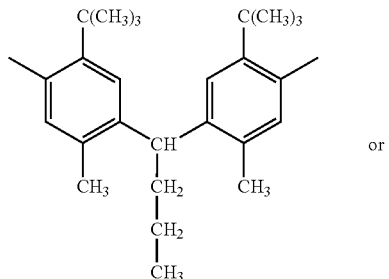 or

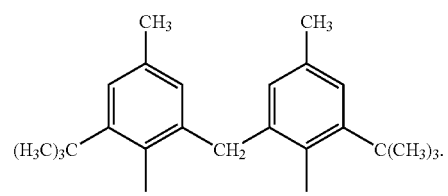

comprising:
(a) heating a 2-phenylphenol compound with a phosphorus trichloride compound in the present of a zinc chloride catalyst to obtain a 6-chloro-6H-dibenz[c,e][1,2]oxaphosphorin of the following formula (II):

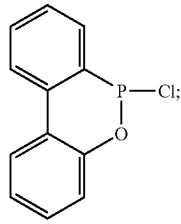
(II)

(b) removing the excess phosphorus trichloride; and
(c) heating an organic solution of a di-hydroxylphenol of the following formula (III), Ar—(OH)$_2$        (III)

wherein Ar is defined the same as the above formula (I), with the 6-chloro-6H-dibenz[c,e][1,2]oxaphosphorin of formula (II) to form the arylphosphonite antioxidant of formula (I).

2. The method as claimed in claim 1, wherein the molar ratio of the 2-phenylphenol compound to the phosphorus trichloride compound in step (a) ranges from 1:1.1 to 1:1.2.

3. The method as claimed in claim 1, wherein the heating temperature in step (a) ranges from 30 to 200° C.

4. The method as claimed in claim 1, wherein the heating temperature in step (c) ranges from 80 to 150° C.

5. The method as claimed in claim 1, wherein the organic solution in step (c) has an organic solvent, which is toluene or chlorobenzene.

* * * * *